(12) United States Patent
Meisenbach et al.

(10) Patent No.: US 11,649,213 B2
(45) Date of Patent: May 16, 2023

(54) SYNTHETIC METHOD FOR THE PREPARATION OF A 3-[5-AMINO-4-(3-CYANOBENZOYL)-PYRAZOL COMPOUND

(71) Applicant: MEREO BIOPHARMA 1 LIMITED, London (GB)

(72) Inventors: Mark Meisenbach, Basel (CH); Benjamin Martin, Basel (CH); Niek Johannes Ronde, Weert (NL); Carmen Ruiz, Weert (NL)

(73) Assignee: MEREO BIOPHARMA 1 LIMITED, London (GB)

(*) Notice: Subject to any disclaimer, the term of this patent is extended or adjusted under 35 U.S.C. 154(b) by 84 days.

(21) Appl. No.: 17/279,553

(22) PCT Filed: Sep. 26, 2019

(86) PCT No.: PCT/GB2019/052718
§ 371 (c)(1),
(2) Date: Mar. 24, 2021

(87) PCT Pub. No.: WO2020/065323
PCT Pub. Date: Apr. 2, 2020

(65) Prior Publication Data
US 2021/0395207 A1 Dec. 23, 2021

(30) Foreign Application Priority Data
Sep. 26, 2018 (GB) ...................... 1815695

(51) Int. Cl.
*C07D 231/38* (2006.01)
(52) U.S. Cl.
CPC .................. *C07D 231/38* (2013.01)
(58) Field of Classification Search
CPC .................................................. C07D 231/38

USPC ....................................................... 548/371.7
See application file for complete search history.

(56) References Cited

U.S. PATENT DOCUMENTS

| | | |
|---|---|---|
| 3,658,838 A | 4/1972 | Kiehne et al. |
| 5,723,483 A | 3/1998 | Labeeuw et al. |
| 2005/0256113 A1 | 11/2005 | Cogan et al. |

FOREIGN PATENT DOCUMENTS

| | | |
|---|---|---|
| CN | 102964270 A | 3/2013 |
| JP | 2007-521278 A | 2/2007 |
| JP | 2009-293016 A | 12/2009 |
| JP | 2010-535187 A | 11/2010 |
| WO | 2005/007632 A1 | 1/2005 |
| WO | 2005/009973 A1 | 2/2005 |
| WO | 2007/083320 A2 | 7/2007 |
| WO | 2009/016414 A1 | 2/2009 |
| WO | 2009/088025 A1 | 7/2009 |
| WO | 2018/059533 A1 | 4/2018 |

OTHER PUBLICATIONS

International Search Report and Written Opinion dated Oct. 30, 2019 in PCT/GB2019/052718 (10 pages).
International Search Report and Written Opinion dated Oct. 30, 2019 in PCT/GB2019/052719 (13 pages).
U.S. Appl. No. 17/279,548, filed Mar. 24, 2021.

*Primary Examiner* — Taofiq A Solola
(74) *Attorney, Agent, or Firm* — Wolff IP a Prof Corp; Jessica Wolff

(57) ABSTRACT

Provided is a process for preparing a compound, comprising the steps of a) Reacting a compound of Formula A (Formula A) with the compound 3 (3) to provide the compound 5 (5) or a salt or solvate thereof, wherein R is a linear or branched C1-C5 alkyl. Further provided is the compound 5 or a salt or solvate thereof. (5) The use of these compounds in the synthesis of 3-[5-Amino-4-(3-Cyanobenzoyl)-Pyrazol-1-yl]-N-Cyclopropyl-4-Methylbenzamide is also provided.

17 Claims, 2 Drawing Sheets

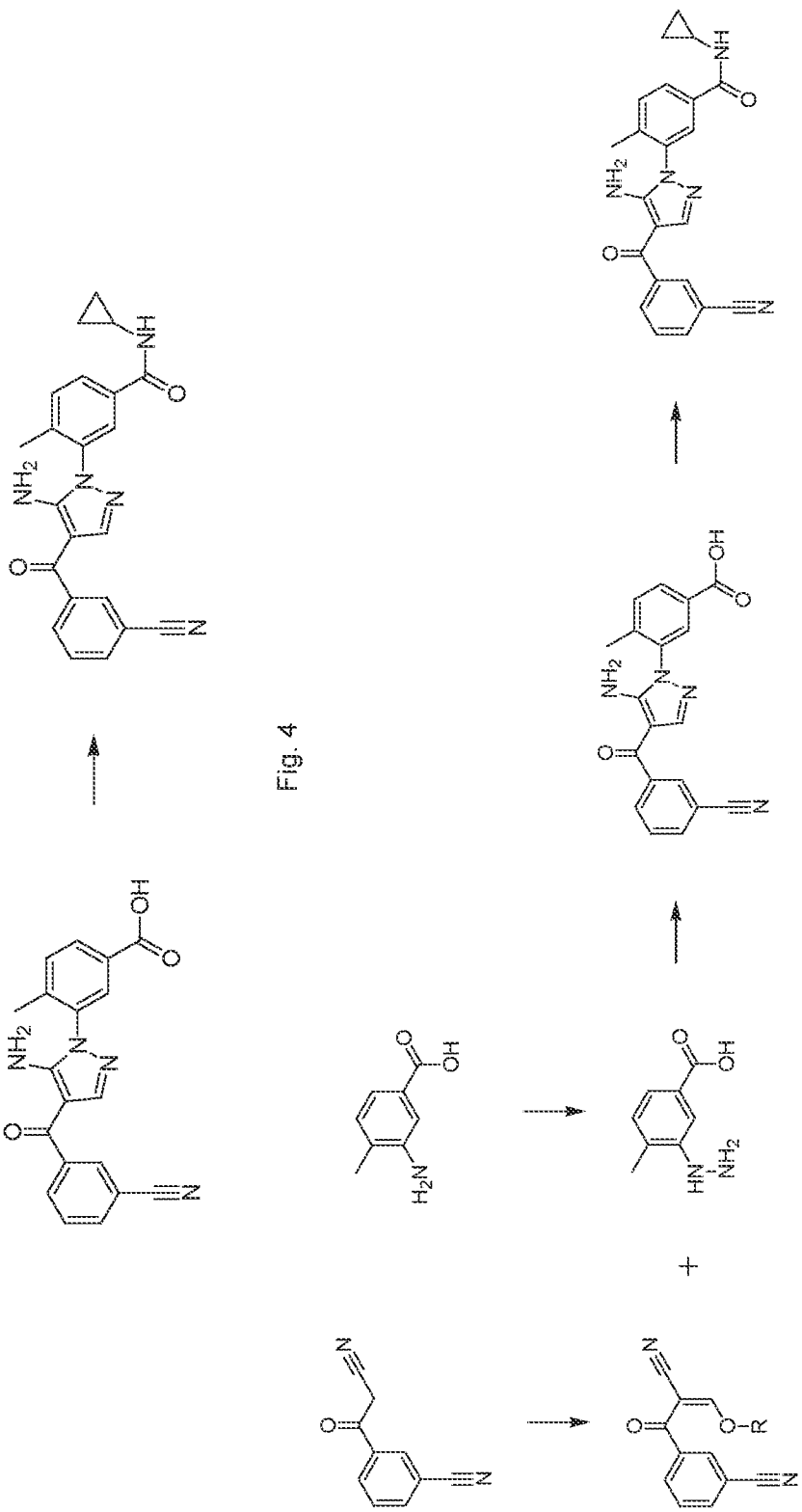

SYNTHETIC METHOD FOR THE PREPARATION OF A 3-[5-AMINO-4-(3-CYANOBENZOYL)-PYRAZOL COMPOUND

CROSS-REFERENCE TO RELATED APPLICATIONS

The present invention is filed under 35 U.S.C. § 371 as the U.S. national phase of International Patent Application No. PCT/GB2019/052718, filed Sep. 26, 2019, which designated the United States, and which claims the benefit of priority to GB Patent Application No. 1815695.0, filed Sep. 26, 2018, each of which is hereby incorporated by reference in its entirety including all tables, figures, and claims.

FIELD OF THE INVENTION

The present invention discloses a novel compound 3-[5-Amino-4-(3-Cyanobenzoyl)-1H-Pyrazol-1-yl]-4-Methylbenzoic Acid and salts and solvates thereof, a process for the production of 3-[5-Amino-4-(3-Cyanobenzoyl)-1H-Pyrazol-1-yl]-4-Methylbenzoic Acid and its use in the synthesis of 3-[5-Amino-4-(3-Cyanobenzoyl)-Pyrazol-1-yl]-N-Cyclopropyl-4-Methylbenzamide.

BACKGROUND OF THE INVENTION

The compound 3-[5-Amino-4-(3-Cyanobenzoyl)-Pyrazol-1-yl]-N-Cyclopropyl-4-Methylbenzamide was first disclosed in international patent application WO2005/009973, amongst various other pyrazole- and imidazole-based compounds that have cytokine inhibitory activity. WO2005/009973 discloses that such compounds can be used to treat conditions associated with p38 kinases, especially p38α and β kinases, including chronic obstructive pulmonary disease. WO2005/009973 discloses 3-[5-Amino-4-(3-Cyanobenzoyl)-Pyrazol-1-yl]-N-Cyclopropyl-4-Methylbenzamide as one such novel pyrazole-based p38 kinase inhibitor. 3-[5-Amino-4-(3-Cyanobenzoyl)-Pyrazol-1-yl]-N-Cyclopropyl-4-Methylbenzamide has the following chemical structure:

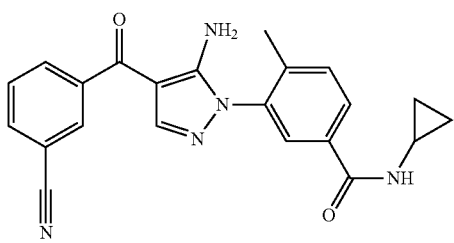 [SMILES: Cc1ccc(C(=O)NC2CC2)cc1-n1ncc(C(=O)c2cccc(C#N)c2)c1N]

WO2005/009973 describes processes for the preparation of 3-[5-Amino-4-(3-Cyanobenzoyl)-Pyrazol-1-yl]-N-Cyclopropyl-4-Methylbenzamide. However, the above processes were not designed with commercial scale production in mind. Consequently there are several problems with the previously disclosed syntheses which render them unsuitable for commercial scale production of 3-[5-Amino-4-(3-Cyanobenzoyl)-Pyrazol-1-yl]-N-Cyclopropyl-4-Methylbenzamide.

Such problems include production of harmful or dangerous by-products, poor control of reactions, e.g. due to highly exothermic reaction thermodynamics or excessive kinetics, complex waste stream management, complex purification procedures, unacceptably impure products and poor yield.

To date, there are no simple methods for the production of 3-[5-Amino-4-(3-Cyanobenzoyl)-Pyrazol-1-yl]-N-Cyclopropyl-4-Methylbenzamide that are suitable for the commercial scale. There is therefore an unmet need to provide efficient methods for the production of 3-[5-Amino-4-(3-Cyanobenzoyl)-Pyrazol-1-yl]-N-Cyclopropyl-4-Methylbenzamide and useful intermediate compounds that are suitable for the commercial scale.

SUMMARY OF THE INVENTION

The present invention provides a process for preparing a compound, comprising the steps of a) Reacting a compound of Formula A

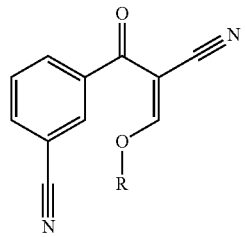

Formula A with the compound 3

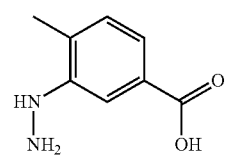

3 to provide the compound 5

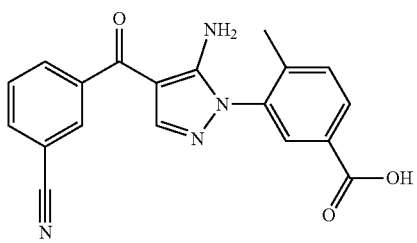

5 or a salt or solvate thereof;

b) Optionally isolating the compound 5 or a salt or solvate thereof; and c) Optionally reacting the compound 5 or a salt or solvate thereof with cyclopropylamine to provide the compound 6 or a salt or solvate thereof

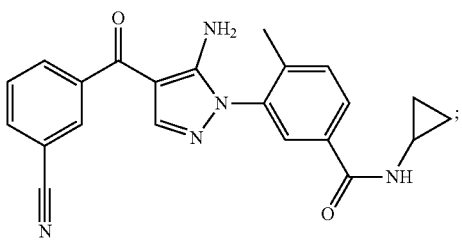

wherein R is a linear or branched C1-C5 alkyl.

The present invention further provides a product obtained by the above process.

The present invention further provides the compound 5

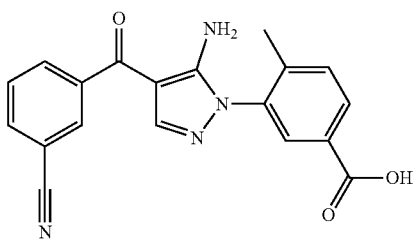

or a salt or solvate thereof.

The present invention further provides the use of a product obtained by the above process or the compound 5 as an intermediate compound in the synthesis of 3-[5-Amino-4-(3-Cyanobenzoyl)-Pyrazol-1-yl]-N-Cyclopropyl-4-Methylbenzamide.

BRIEF DESCRIPTION OF DRAWINGS

Certain aspects of the embodiments described herein may be more clearly understood by reference to the drawings, which are intended to illustrate, but not limit, the invention, and wherein:

FIG. 4 is a scheme showing an exemplary process for the conversion of compound 5 into 3-[5-Amino-4-(3-Cyanobenzoyl)-Pyrazol-1-yl]-N-Cyclopropyl-4-Methylbenzamide in accordance with the invention.

FIG. 5 is a scheme showing an exemplary process for the total synthesis of 3-[5-Amino-4-(3-Cyanobenzoyl)-Pyrazol-1-yl]-N-Cyclopropyl-4-Methylbenzamide in accordance with the invention.

DETAILED DESCRIPTION OF THE INVENTION

Figures 1, 2, 3:
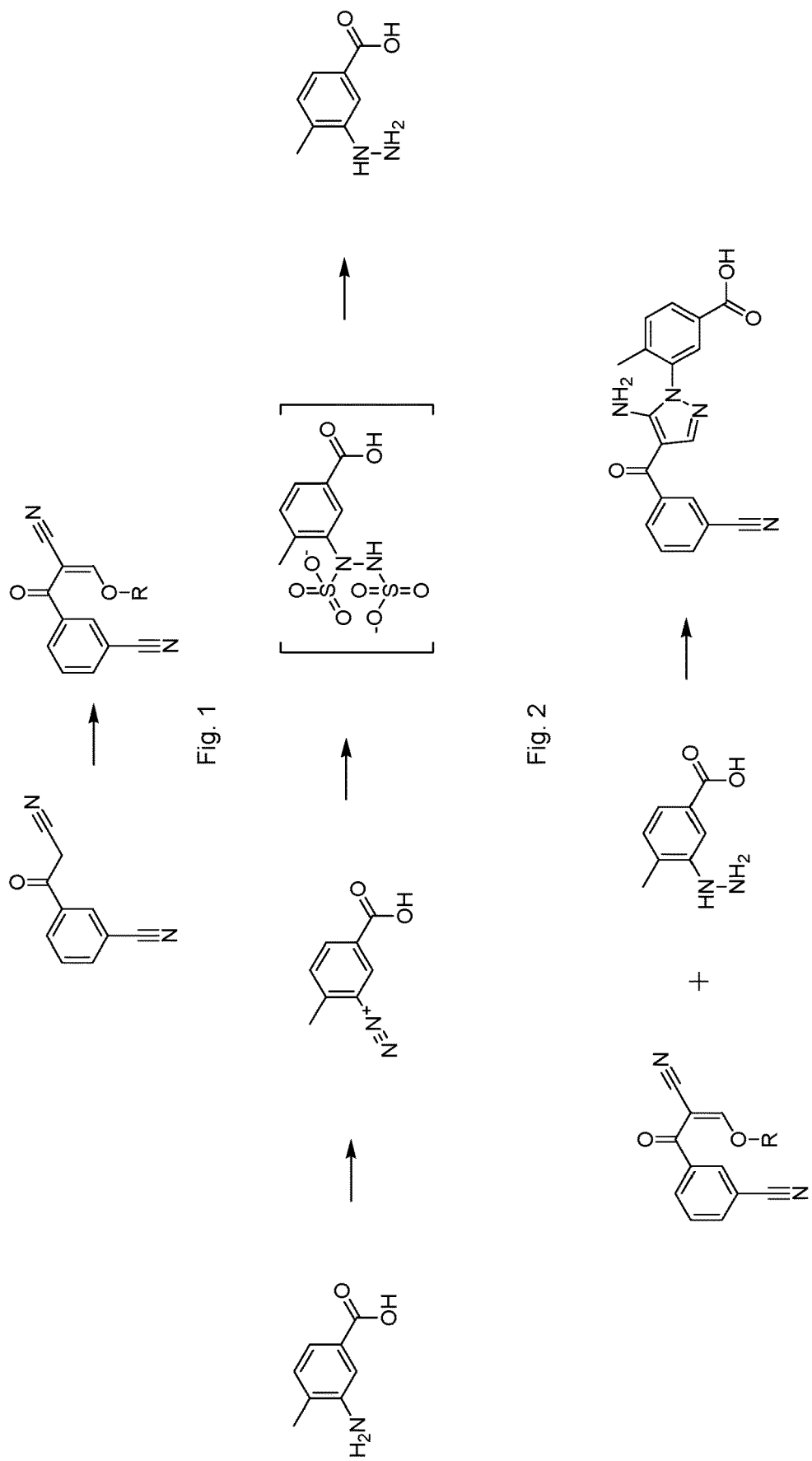
FIG. 1 is a scheme showing an exemplary process for the conversion of compound 1 into compounds of Formula A in accordance with the invention.
FIG. 2 is a scheme showing an exemplary process for the conversion of compound 4 into compound 3 in accordance with the invention. Compound 4 is first converted into a diazonium salt, then to a hydrazyl sulfite complex, which is subsequently hydrolysed to provide compound 3.
FIG. 3 is a scheme showing an exemplary process for the production of compound 5 from compound 3 and a compound of Formula A in accordance with the invention.

The present invention provides methods and intermediate compounds useful in the production of 3-[5-Amino-4-(3-Cyanobenzoyl)-Pyrazol-1-yl]-N-Cyclopropyl-4-Methylbenzamide. It will be appreciated that the described methods may be combined with other steps and methods not described herein in order to provide 3-[5-Amino-4-(3-Cyanobenzoyl)-Pyrazol-1-yl]-N-Cyclopropyl-4-Methylbenzamide. It will also be appreciated that the methods described below may be combined to provide a complete synthetic route to 3-[5-Amino-4-(3-Cyanobenzoyl)-Pyrazol-1-yl]-N-Cyclopropyl-4-Methylbenzamide.

It will be appreciated that when specific compounds such as compounds of Formula A, 1, 2, 3, 4, 5 or 6 are mentioned herein, unless the context requires otherwise, salts and solvates thereof are intended to be within the scope of the invention.

The starting material for any aspects of the invention may be any source. For example the starting material may be a crude product from a previous reaction, or the starting material may be a pure product, either commercially obtained or through purifying a crude product from a previous reaction.

For all synthetic steps described, after conventional work-up, the crude products may be purified, if necessary, by conventional purification methods, such as chromatography, trituration, crystallization or preparative HPLC.

The methods of the present invention are preferably used for large scale production (greater than 5 kg) of material.

As used herein, pure or highly pure means a purity of greater than 80 wt % of the material, or greater than 90 wt %, preferably greater than 95 wt %, for example, greater than 98 wt %. Those skilled in the art know of methods for the determination of purity. For example, purity may be determined by HPLC, such as assay (% w/w) or area percent (area %), and typically employs the use of reverse-phase chromatography using an aqueous based mobile phase and either methanol or acetonitrile.

It will be appreciated that when methods according to the invention mention a step of adding one component to another, unless the context requires otherwise, the addition of either component to the other component is intended to be within the scope of the invention.

In accordance with the invention compounds of Formula A

Formula A

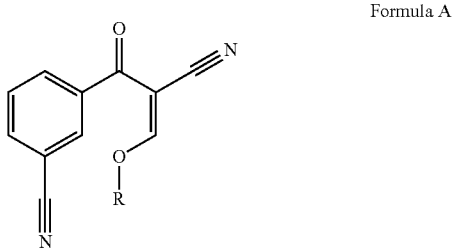

or salts or solvates thereof may be prepared by a process comprising the step of
a) Reacting the compound 1

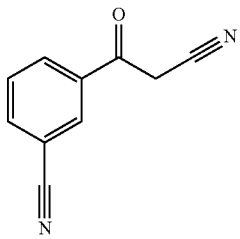

1 with a trialkyl orthoformate to provide a compound of Formula A or a salt or solvate thereof,
wherein R is the alkyl moiety of the trialkyl orthoformate.

The compound of Formula A may be isolated from the reaction mass or the crude product, for example in solution, may be used in a subsequent reaction. For example, the crude product may be used in the reaction between compounds of Formula A and the compound 3, described in detail below.

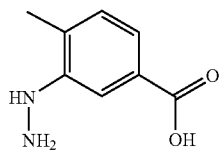

3

3-hydrazino-4-methyl-benzoic acid

According to the invention an alkoxymethylidene of Formula A may be produced by reacting the compound 1 with a trialkyl orthoformate. Compounds according to the Formula A are useful intermediate compounds in the production of 3-[5-Amino-4-(3-Cyanobenzoyl)-Pyrazol-1-yl]-N-Cyclopropyl-4-Methylbenzamide. Cyclisation of compounds of Formula A with the compound 3 produces the key pyrazole intermediate compound 5 and alcohol by-products.

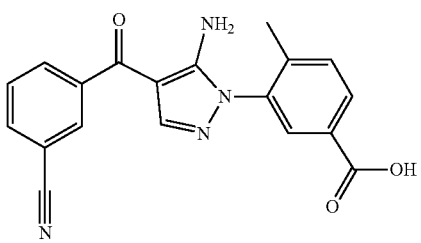

5

3-[5-Amino-4-(3-Cyanobenzoyl)-1H-Pyrazol-1-yl]-4-Methylbenzoic Acid

Previous processes to provide pyrazoles similar to compound 5, such as those disclosed in WO2005/009973, were found to produce harmful by-products such as aniline. By using a trialkyl orthoformate to produce an alkoxymethyl-idene of Formula A, subsequent cyclisation of the compound of Formula A with the compound 3 eliminates an alcohol, which is a preferred by-product in terms of safety.

An additional problem with previous processes to provide pyrazoles similar to compound 5 is the control of the cyclisation reaction. The cyclisation reaction disclosed in WO2005/009973 to produce a pyrazole has been found to involve a sharp exothermic reaction profile, which may render the reaction unsuitable for commercial scale production. The present invention solves this problem by providing a reaction with a slower rate, which is facile to control and avoids the safety concerns associated with a sharp exothermic reaction profile. In addition, a slower reaction rate is desirable as it affords enhanced control of the reaction and reduces the production of impurities.

Therefore the invention enables safe production of key intermediate compound 5 and 3-[5-Amino-4-(3-Cyanobenzoyl)-Pyrazol-1-yl]-N-Cyclopropyl-4-Methylbenzamide on a commercial scale.

Reacting the compound 1 with a trialkyl orthoformate to provide a compound of Formula A may comprise one or more or all of the following steps
a) Adding the compound 1 in an aprotic solvent;
b) Optionally adding to the reaction mass an organic acid anhydride;
c) Distilling the reaction mass;
d) Adding the trialkyl orthoformate to the reaction mass during distillation to provide a compound of Formula A;
e) Optionally cooling the reaction mass, preferably to less than about 25° C.;
f) Optionally adding an antisolvent to the reaction mass;
g) Optionally further cooling the reaction mass to about 0 to about 5° C.;
h) Optionally filtering the compound of Formula A,
i) Optionally washing the filtrate with the antisolvent; and
j) Optionally drying the filtrate.

In one embodiment isolating the compound of Formula A comprises steps (h)-(j) described above.

The reaction of compound 1 with a trialkyl orthoformate may produce an alcohol by-product. The alcohol by-product may be predicted from the trialkyl orthoformate used in the reaction, for example triethyl orthoformate may produce ethanol as the by-product alcohol. It is preferable to remove alcohol by-products during the reaction of the trialkyl orthoformate with the compound 1. The removal of the alcohol by-product facilitates the reaction conversion to the compound 2. It has been found that removal of alcohol by-products allows improved yield. In one embodiment removal of alcohol by-products is achieved by distilling the reaction mass containing compound 1 in an aprotic solvent and adding the trialkyl orthoformate to the reaction mass during distillation. In another embodiment removal of alcohol by-products is achieved by addition of an organic acid anhydride, such as acetic anhydride, to the reaction mass. These embodiments may be combined to further enhance removal of alcohol by-products to allow further improved yield.

An organic acid anhydride is a compound consisting of two acyl groups bonded to the same oxygen atom, acyl-O-acyl. Symmetric and mixed anhydrides which have identical and different acyl groups, respectively, are contemplated herein. The organic acid anhydride may be selected from the group consisting of acetic anhydride, propionic anhydride, butyric anhydride, acetic propionic anhydride and acetic butyric anhydride, preferably is acetic anhydride.

The trialkyl orthoformate may be a linear or branched C1-C5 trialkyl orthoformate, in which case R may be a linear or branched C1-C5 alkyl. The trialkyl orthoformate may be selected from the group consisting of trimethyl orthoformate, triethyl orthoformate, tripropyl orthoformate, tributyl orthoformate and tripentyl orthoformate.

The trialkyl orthoformate may be triethyl orthoformate, in which case Formula A is the compound 2.

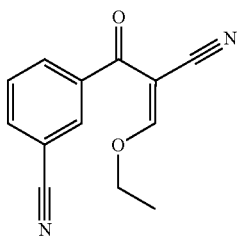

2

3-[2-Cyano-2-(Ethoxymethylidene)Acetyl]Benzonitrile

The reaction of a trialkyl orthoformate, such as triethyl orthoformate, with the compound 1 may produce an alcohol, such as ethanol, as a by-product. In this reaction ethanol is a preferred by-product as it is highly volatile and forms azeotropic mixtures with certain solvents, such as toluene and cyclohexane, which facilitates its elimination and the purification of the compound of Formula A. The use of triethyl orthoformate leads to improved yield over prior processes.

In addition, triethyl orthoformate is a preferred reagent because subsequent cyclisation of compound 2 with compound 3 produces the key pyrazole intermediate compound 5 and ethanol as a by-product. Ethanol is a preferred by-product as it is highly volatile, which facilitates its elimination and the purification of the compound 5. The use of the compound 2 leads to improved yield over prior processes. Ethanol also possesses an acceptable toxicological profile in the event of product contamination.

An aprotic solvent is a solvent that is not a hydrogen bond donor. The aprotic solvent may be selected from the group consisting of toluene, cyclohexane and xylene. The reaction of a trialkyl orthoformate, such as triethyl orthoformate, with the compound 1 may produce an alcohol, such as ethanol, as a by-product. The aprotic solvent preferably forms an azeotropic mixture with the alcohol by-product. This facilitates elimination of the alcohol by-product and purification of the compound of Formula A. As the alcohol by-product may be predicted from the trialkyl orthoformate used in the reaction, for example triethyl orthoformate may produce ethanol as the by-product alcohol, those skilled in the art will be able to select appropriate aprotic solvents which form an azeotrope with the by-product alcohol. Preferably the aprotic solvent is toluene or cyclohexane, especially when triethyl orthoformate is used. It is known that toluene and cyclohexane form azeotropic mixtures with ethanol. The inventors have found that formation of an azeotropic mixture facilitates elimination of ethanol and purification of the compound 2. Furthermore, the removal of the alcohol by-product facilitates the reaction conversion to the compound 2. Preferably the aprotic solvent is toluene.

The step of distilling the reaction mass may comprise distilling the reaction mass at about 60° C. to about 130° C. under vacuum, such as at about 500 mBar to about 1 Bar. Preferably the reaction mass is distilled at about 105° C. and about 800 to about 900 mBar. It will be appreciated that those skilled in the art will be able to select appropriate conditions for distillation and that distillation in the present invention includes reflux.

As used herein, an antisolvent is a solvent in which a compound of Formula A is insoluble or poorly soluble in, for example less than 5 wt %, or less than 1 wt %, or even less than 0.1 wt % soluble. It will be appreciated that those skilled in the art will be able to select appropriate antisolvents for given compounds of Formula A. The antisolvent may be selected from the group consisting of pentane, hexane, cyclohexane, heptane and distillation fractions thereof, and unless the context demands otherwise, all isomers thereof are intended to be within the scope of the invention. Preferably the antisolvent is n-heptane.

In accordance with the invention a product may be obtained by the above-described process.

In accordance with the invention the compound 2, 3-[2-Cyano-2-(Ethoxymethylidene)Acetyl]Benzonitrile, or a salt or solvate thereof is provided.

The present invention further provides the use of a product obtained by the above process or the compound 2 as an intermediate compound in the synthesis of 3-[5-Amino-4-(3-Cyanobenzoyl)-Pyrazol-1-yl]-N-Cyclopropyl-4-Methylbenzamide.

In accordance with the invention the compound 3

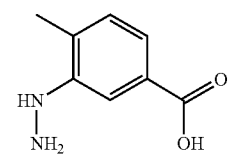

3 or a salt or a solvate thereof may be produced by a process comprising the steps of a) Mixing the compound 4 with a mineral acid

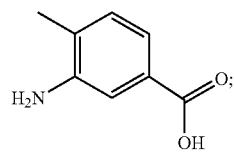

4 b) Adding a nitrite salt or an organic nitrite derivative to the reaction mass to form a diazonium salt;
c) Adding a sulfur-containing reducing agent to the reaction mass to form a hydrazyl sulfur complex, such as a hydrazyl sulfite complex;
d) Hydrolysing the hydrazyl sulfur complex to provide the compound 3; and
e) Optionally isolating the compound 3 or a salt or solvate thereof.

The compound 3 may be isolated from the reaction mass. For example, the crude product may be purified to produce a pure form of compound 3 that may be used in the reaction between compounds of Formula A and the compound 3, described in detail below.

In one embodiment isolating the compound 3 comprises filtering the compound 3, washing the filtrate with water and optionally drying the filtrate.

Methods of filtering are known to those skilled in the art. Exemplary methods include filter drying apparatus, centrifugal filtration and membrane filtration.

According to the invention, the compound 4 is converted into the compound 3 using a nitrite salt or an organic nitrite derivative to form a diazonium salt, followed by subsequent reduction of the diazonium salt by a sulfur-containing reducing agent to form a hydrazyl sulfur complex, such as a hydrazyl sulfite complex. Hydrolysis of the hydrazyl sulfur complex provides the compound 3. Compound 3 is a key intermediate compound in the synthesis of 3-[5-Amino-4-(3-Cyanobenzoyl)-Pyrazol-1-yl]-N-Cyclopropyl-4-Methylbenzamide. Previously available methods of producing the compound 3 have been found to be too complex and expensive to be suitable for scale-up. There is therefore an unmet need to provide a process of producing the compound 3 that is suitable for the commercial scale.

Nitrite salts such as sodium nitrite and organic nitrite derivatives such as alkyl nitrites are suitable for use on a commercial scale. Nitrite salts are readily available reagents and have an acceptable toxicological profile in the event of final product contamination.

Some previous methods of converting aniline derivatives to hydrazine derivatives, such as those employing triphenylphosphine, are not suitable for the commercial scale due to complexities in handling the waste streams of those processes. For example, the negative effects of phosphorus-containing waste, such as eutrophication, are well-documented. The present invention solves this problem by providing a process that does not require the use of phosphorus-containing reagents to provide the compound 3.

The inventors have also found that previous methods of converting aniline derivatives to hydrazine derivatives require complex isolation and purification steps to provide an acceptably pure product. These inefficiencies are believed to decrease the yield of the desired product. The use of sulfur-containing reducing agents, such as sodium sulfite, and nitrite salts or organic nitrite derivatives, such as sodium nitrite, affords a facile synthesis of the compound 3 which produces waste streams that may be managed on the commercial scale. In addition, the process according to the invention is found to produce by-products that are effectively removed, resulting in a high purity product.

In previous syntheses of the compound 3-[5-Amino-4-(3-Cyanobenzoyl)-Pyrazol-1-yl]-N-Cyclopropyl-4-Methylbenzamide, stannous chloride was used to convert the compound 4 into the compound 3. However, use of stannous chloride was found to result in contamination with tin-containing impurities which must be removed to provide an acceptable product. Removal of tin-containing impurities may be performed through several methods including filtration over silica gel. However, it was found that additional purification steps led to a decrease in product yield. The presently claimed process allows for the elimination of stannous chloride from the overall synthesis of 3-[5-Amino-4-(3-Cyanobenzoyl)-Pyrazol-1-yl]-N-Cyclopropyl-4-Methylbenzamide, thus eliminating the risk of tin-containing impurities contaminating the final product. In addition to benefits in terms of reduced contamination and improved product safety, the presently claimed process allows for improved yield by reducing product loss, for example due to additional purification steps used in previous syntheses.

The compound 3 or a salt or a solvate thereof may be produced by a process comprising one or more or all of the following steps
a) Mixing the compound 4 with a mineral acid;
b) Optionally cooling the reaction mass, preferably to less than about 10° C.;
c) Adding a nitrite salt or an organic nitrite derivative to the reaction mass to form a diazonium salt, preferably at a temperature of less than about 10° C.
d) Adding a sulfur-containing reducing agent to the reaction mass, preferably at a temperature of less than about 10° C.;
e) Optionally heating the reaction mass, preferably to greater than about 50° C., more preferably to about 60° C.;
f) Optionally further heating the reaction mass to greater than about 60° C., preferably to about 80° C.;
g) Hydrolysing the hydrazyl sulfur complex to provide the compound 3, preferably by adding a mineral acid to the reaction mass;
h) Optionally cooling the reaction mass, preferably to less than about 30° C., preferably to about 20 to about 30° C., more preferably to about 25° C.;
i) Optionally adjusting the pH of the reaction mass to about 5 to about 7, preferably about 5.6 to about 5.8;
j) Optionally filtering the compound 3;
k) Optionally washing the filtrate with water;
l) Optionally drying the filtrate;
m) Optionally reslurrying (mixing) the dried filtrate in water;
n) Optionally isolating the compound 3;
o) Optionally washing the compound 3 with water; and
p) Optionally drying the compound 3.

The mineral acid may be selected from the group consisting of HCl, $H_2SO_4$, $HNO_3$, $H_3PO_4$, $HBF_4$ and HBr. Preferably the mineral acid is HCl.

In the reaction the compound 4 is reacted with a nitrite source to form a diazonium salt. The nitrite source is a nitrate salt or an organic nitrite derivative.

The nitrite salt maybe selected from the group consisting of alkali metal nitrite salts, alkaline earth metal nitrite salts and silver nitrite. Exemplary alkali metal nitrite salts include lithium nitrite, sodium nitrite and potassium nitrite. Exemplary alkaline earth metal nitrite salts include magnesium nitrite and calcium nitrite.

An organic nitrite derivative is an organic compound having the formula R—ONO. The organic nitrite derivative may be an alkyl nitrite, such as a linear or branched C1-C5 nitrite. The organic nitrite derivative may be selected from the group consisting of ethyl nitrite, propyl nitrite, butyl nitrite and pentyl nitrite.

Preferably the nitrite source is sodium nitrite.

The sulfur-containing reducing agent may be selected from the group consisting of sulfite salts, bisulfite salts and dithionite salts. Exemplary sulfite salts include alkali metal sulfite salts, such as lithium sulfite, sodium sulfite and potassium sulfite; alkaline earth metal sulfite salts, such as magnesium sulfite and calcium sulfite; and silver sulphite. Exemplary bisulfite salts include alkali metal bisulfite salts, such as sodium bisulfite and potassium bisulfite; and alkaline earth metal bisulfite salts such as calcium bisulfite. An exemplary dithionite salt is sodium dithionite.

Preferably the sulfur-containing reducing agent is sodium sulfite.

In one embodiment, after hydrolysing the hydrazyl sulfur complex to provide the compound 3, the pH of the reaction mass is adjusted to about 5 to about 7, preferably about 5.6 to about 5.8. Without wishing to be bound by theory, it is believed that this step eliminates the production of certain undesirable salt by-products, leading to a higher purity product.

In one embodiment, after adding a sulfur-containing reducing agent to the reaction mass, the reaction mass is heated, preferably to greater than about 50° C., more preferably to about 60° C. The reaction mass may be subsequently further heated to greater than about 60° C., preferably to about 80° C. The reaction mass may be subsequently cooled, preferably to less than about 30° C., preferably to about 20 to about 30° C., more preferably to about 25° C. It was found that cooling the reaction mass to about 20 to about 30° C. before the compound 3 is isolated, such as before the pH of the reaction mass is adjusted, leads to improved product purity. Without wishing to be bound by theory, it is believed that this step eliminates the production of certain undesirable salt by-products, leading to a higher purity product.

In one embodiment, the crude filtrate is reslurried (mixed) in water, then the compound 3 is isolated, washed with water and optionally dried. In this embodiment, isolating the compound 3 may comprise filtering the compound 3. The inventors have found that this additional processing step significantly improves the removal of impurities such as salt by-products, leading to a higher purity product.

In accordance with the invention a product may be obtained by the above-described process.

The present invention further provides the use of a product obtained by the above process as an intermediate compound in the synthesis of 3-[5-Amino-4-(3-Cyanobenzoyl)-Pyrazol-1-yl]-N-Cyclopropyl-4-Methylbenzamide.

In accordance with the invention a compound may be produced by a process comprising the steps of a) Reacting a compound of Formula A

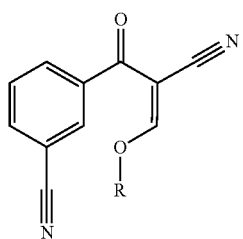

Formula A with the compound 3

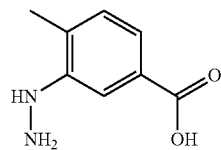

3 to provide the compound 5

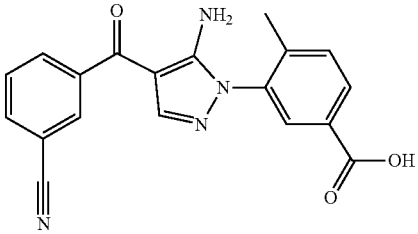

5 or a salt or solvate thereof, wherein R is a linear or branched C1-C5 alkyl.

The process may further comprise one or both of the following steps
b) Isolating the compound 5 or a salt or solvate thereof; and
c) Reacting the compound 5 with cyclopropylamine to provide the compound 6 or a salt or solvate thereof

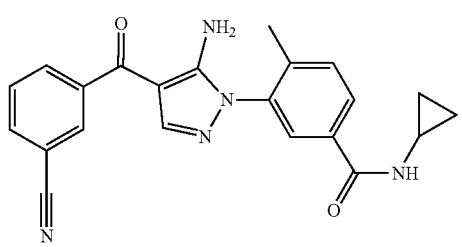

6

3-[5-Amino-4-(3-Cyanobenzoyl)-Pyrazol-1-yl]-N-Cyclopropyl-4-Methylbenzamide

In one embodiment isolating the compound 5 comprises filtering the compound 5, washing the filtrate with water and drying the filtrate. Isolating the compound 5 may further comprise washing the filtrate with methanol after washing the filtrate with water.

The compound of Formula A may be from any source. For example the material may be a crude product from a previous reaction, or the material may be a pure product, either commercially obtained or through purifying a crude product from a previous reaction. Mixtures of crude and pure products are also contemplated. For example, the source of Formula A may be a crude product from the reaction of the compound 1 with a trialkyl orthoformate as described above, or the source may be a pure form of Formula A. It will be appreciated that the skilled person will know appropriate means for obtaining the crude product of previous reactions for use in further reactions, for example for use in a one-pot synthesis or a telescoping synthesis.

The source of compound 3 may be a pure form of compound 3. In one embodiment the source of compound 3 has a water content of less than 1% as determined by Karl Fischer titration. The source of compound 3 may be obtained commercially, or through purifying a crude product from a previous reaction, for example from the conversion of compound 4 to compound 3 as described above. It will be appreciated that the skilled person will know appropriate means for purifying a crude product to be suitable for use in further reactions.

According to the invention the compound 5 is produced by reacting a compound of Formula A with the compound 3. The compound 5 is a key intermediate compound in the production of 3-[5-Amino-4-(3-Cyanobenzoyl)-Pyrazol-1-yl]-N-Cyclopropyl-4-Methylbenzamide.

Cyclisation of compounds of Formula A with the compound 3 produces the key pyrazole intermediate compound 5 and alcohol by-products. Previous processes to provide pyrazoles similar to compound 5, such as those disclosed in WO2005/009973, were found to produce harmful by-products such as aniline. The reaction of compounds of Formula A with the compound 3 eliminates an alcohol, which is a preferred by-product in terms of safety.

An additional problem with previous processes to provide pyrazoles similar to compound 5 is the control of the cyclisation reaction. The cyclisation reaction disclosed in WO2005/009973 to produce a pyrazole has been found to involve a sharp exothermic reaction profile, which may render the reaction unsuitable for commercial scale production. The present invention solves this problem by providing a reaction with a slower rate, which is facile to control and avoids the safety concerns associated with a sharp exothermic reaction profile. In addition, a slower reaction rate is desirable as it affords enhanced control of the reaction and reduces the production of impurities.

Therefore the presently claimed process enables safe production of key intermediate compound 5 and 3-[5-Amino-4-(3-Cyanobenzoyl)-Pyrazol-1-yl]-N-Cyclopropyl-4-Methylbenzamide on a commercial scale.

In one embodiment, R may be $C_2H_5$, in which case Formula A is the compound 2, 3-[2-Cyano-2-(Ethoxymethylidene)Acetyl]Benzonitrile.

The compound 2 is a preferred reagent because cyclisation of compound 2 with compound 3 produces the key pyrazole intermediate compound 5 and ethanol as a by-product. Ethanol is a preferred by-product as it is highly volatile, which facilitates its elimination and the purification of intermediate compound 5. Without wishing to be bound by theory, it is believed that use of the compound 2 leads to improved yield over prior processes. Ethanol also possesses an acceptable toxicological profile in the event of product contamination.

The compound 5 may be produced by a process comprising one or more or all of the steps of
a) Adding the compound of Formula A to the compound 3 in a polar aprotic solvent, optionally under anhydrous conditions, optionally at a temperature of greater than about 90° C., preferably at about 105° C. to provide the compound 5 or a salt or solvate thereof;
b) Optionally cooling the reaction mass, preferably to less than about 70° C., more preferably to about 60° C.;
c) Optionally adding water to the reaction mass;
d) Optionally further cooling the reaction mass, preferably to less than about 30° C., more preferably to about 20° C.;
e) Optionally filtering the compound 5;
f) Optionally washing the filtrate with water;
g) Optionally washing the filtrate with methanol; and
h) Optionally drying the filtrate,
wherein R is a linear or branched C1-C5 alkyl.

The process may further comprise the step of reacting the compound 5 with cyclopropylamine to provide the compound 6. Reacting the compound 5 with cyclopropylamine to provide the compound 6 may comprise one or more or all of the following steps a) Adding the compound 5 to a polar aprotic solvent;
b) Heating the above reaction mass, preferably to a temperature greater than about 30° C., more preferably to about 40° C.;
c) Optionally adding a coupling reagent in a polar aprotic solvent;
d) Optionally purging the reaction vessel, preferably to remove $CO_2$;
e) Adding cyclopropylamine to the reaction mass;
f) Maintaining the reaction mass to provide the compound 6;
g) Optionally cooling, preferably to less than about 30° C., more preferably to about 25° C.;
h) Optionally adding water to the reaction mass;
i) Optionally filtering the compound 6;
j) Optionally washing the filtrate with water; and
k) Optionally drying the filtrate.

After isolating the compound 6, which in one embodiment comprises steps (i)-(k) described above, the compound 6 may be subsequently recrystallized with a polar aprotic solvent/water recrystallization. The inventors have found that this recrystallization step affords greater consistency in product quality for the final product.

In the reaction of Formula A with the compound 3 and subsequent conversion of compound 5 to compound 6, the polar aprotic solvent may be selected from the group consisting of dimethyl sulfoxide, dimethylacetamide, dimethylformamide and N-methyl-2-pyrrolidone. Preferably the polar aprotic solvent is dimethyl sulfoxide. Dimethyl sulfoxide is readily available and particularly suitable for use on the commercial scale.

In one embodiment the coupling agent that may be used is selected from the group consisting of CDI, HOBt and HATU, preferably CDI. The atom economy of the reaction using CDI is significantly greater than similar reactions which employ different coupling agents. In addition, CDI is readily available and particularly suitable for use on the commercial scale.

In accordance with the invention a product may be obtained by the above-described process.

In accordance with the invention the compound 5, 3-[5-Amino-4-(3-Cyanobenzoyl)-1H-Pyrazol-1-yl]-4-Methylbenzoic Acid, or a salt or solvate thereof is provided.

The present invention further provides the use of a product obtained by the above process or the compound 5 as an intermediate compound in the synthesis of 3-[5-Amino-4-(3-Cyanobenzoyl)-Pyrazol-1-yl]-N-Cyclopropyl-4-Methylbenzamide.

The invention will now be described further by reference to the following examples, which are intended to illustrate, but not limit, the scope of the appended claims.

EXAMPLES

Example 1

The process is described relative to the intake of compound 1 (1.0 eq).

Acetic anhydride (2.0 eq) was added to a mixture of 3-(cyanoacetyl)benzonitrile (compound 1) (1.0 eq) in toluene (4.5 vol) and heated to 105° C. The pressure was reduced to 800-900 mbar slowly until slight reflux was obtained. Triethyl orthoformate (1.5 eq) was added during distillation. The reaction was post stirred for 1 h. The reaction was cooled to 25° C. and the product crystallized. n-heptane (5 vol) was added over 0.5 h. The reaction was further cooled to below 5° C. and stirred for 1 h. The product was filtered off, washed with n-heptane (2×2 vol) and dried under vacuum. 3-[2-Cyano-2-(Ethoxymethylidene)Acetyl] Benzonitrile (compound 2) was obtained as a red solid in 90% yield with a purity of 98% (HPLC, area %).

Example 2

The process is described relative to the intake of compound 4 (1.0 eq).

Hydrochloric acid (30%, 3.7 eq) was added to a suspension of 3-amino-4-methylbenzoic acid (compound 4) (1.0 eq) in water (1.5 vol). The suspension was cooled to below 10° C. and stirred for 0.5 h. A solution of sodium nitrite (1.1 eq) in water (0.85 vol) was added slowly while maintaining the temperature below 10° C. The reaction was post-stirred for 0.5 h. A cooled (<5° C.) suspension of sodium sulfite (4.9 eq) in water (10 vol) was added to the reaction mixture at maintaining the temperature below 15° C. The reaction was post-stirred for 1 h. The resulting mixture was heated to 60° C. for 1 h. Hydrochloric acid (30%, 7.2 eq) was added and the mixture was stirred at 80° C. for 2 h. The mixture was cooled to 25° C. Aqueous sodium hydroxide (33%) was added (final pH: 5.6-5.8). The mixture was post-stirred for 1 h, filtered, washed with water (2×4 vol) and dried under vacuum to obtain 3-hydrazino-4-methyl-benzoic acid (compound 3) in 63% yield with a purity of 87% (HPLC, w/w %).

The filter cake was reslurried in water (6 vol) at 25° C. for 1 h. The mixture was filtered, washed with water (2×4 vol) and dried under vacuum to obtain 3-hydrazino-4-methyl-benzoic acid (compound 3) in 61% yield with a purity of 96% (HPLC, area %).

Example 3

The process is described relative to the intake of compound 2 (1.0 eq).

A solution of 3-[2-Cyano-2-(Ethoxymethylidene)Acetyl] Benzonitrile (compound 2) (1.0 eq) in dimethyl sulfoxide (4 vol) was added to a solution of 3-hydrazino-4-methyl-benzoic acid (compound 3) (1.2 eq) in dimethyl sulfoxide (20 vol) at 105° C. in 1.5 h. The reaction was post-stirred for 1 h. Water (24 vol) was added at 60° C. over 1 h and the mixture was subsequently cooled to 20° C. The mixture was post-stirred for 1 h, filtered, washed with water (2 vol), washed with cold methanol (<5° C., 2×4 vol) and dried under vacuum. 3-[5-Amino-4-(3-Cyanobenzoyl)-1H-Pyrazol-1-yl]-4-Methylbenzoic Acid (compound 5) was obtained as a light yellow solid in 52% yield with a purity of 98% (HPLC, area %).

Example 4

The process is described relative to the intake of compound 2 (1.0 eq).

A solution of 3-[2-Cyano-2-(Ethoxymethylidene)Acetyl] Benzonitrile (compound 2) (1.0 eq) in dimethyl sulfoxide (4 vol) was added to a solution of 3-hydrazino-4-methyl-benzoic acid (compound 3) (1.2 eq) in dimethyl sulfoxide (20 vol) at 105±5° C. in 1.25±0.25 h. The reaction was post-stirred for approximately 1 h. The temperature of the mixture was adjusted to 60±5° C. Water (24 vol) was added to the mixture at 60±5° C. over a period of 1±0.25 h. The temperature of the mixture was adjusted to 20±5° C. The mixture was post-stirred for 1.5±0.5 h then filtered. The filtrate was mixed with water (2 vol) at 20±5° C. then filtered and dried under vacuum. 3-[5-Amino-4-(3-Cyanobenzoyl)-1H-Pyrazol-1-yl]-4-Methylbenzoic Acid (compound 5) was obtained.

Example 5

The process is described relative to the intake of compound 5 (1.0 eq).

1,1'-Carbonyldiimidazole (CDI) (1.3 eq) in DMSO (5 vol) was dosed to a suspension of 3-[5-Amino-4-(3-Cyanobenzoyl)-1H-Pyrazol-1-yl]-4-Methylbenzoic Acid (compound 5) (1.0 eq) in DMSO (5 vol) at 40° C. The reaction was post-stirred for 1 h. The formed $CO_2$ was removed by vacuum. Cyclopropylamine (1.2 eq) in DMSO (2 vol) was added to the mixture at 40° C. in 1 h. The mixture was cooled to 25° C. Water (6 vol) was added in 0.5 h. If crystals were not obtained, water (4 vol) was added in 0.25 h. The mixture was post-stirred for 2 h, filtered, washed with water (2×1 vol) and dried under vacuum. 3-[5-Amino-4-(3-Cyanobenzoyl)-Pyrazol-1-yl]-N-Cyclopropyl-4-Methylbenzamide was obtained as yellow solid in 91% yield with a purity of 98% (HPLC, area %).

Example 6

The process is described relative to the intake of compound 5 (1.0 eq).

A suspension of 3-[5-Amino-4-(3-Cyanobenzoyl)-1H-Pyrazol-1-yl]-4-Methylbenzoic Acid (compound 5) (1.0 eq) in DMSO (6.5 vol) was added to a solution of 1,1'-Carbonyldiimidazole (CDI) (1.3 eq) in DMSO (5 vol) at 40±5° C. over a period of approximately 0.5 h. The reaction was post-stirred for 1.25±0.25 h. The formed $CO_2$ was removed by vacuum. Cyclopropylamine (1.2 eq) was added to the mixture at 40±5° C. over a period of approximately 0.5 h. The reaction was post-stirred for 3±1 h. The temperature of the mixture was adjusted to 30±5° C. Water (16.8 vol) was added in 1.5±0.5 h. The temperature of the mixture was adjusted to 20±5° C. over a 2.5±0.5 h period. The mixture was post-stirred for 8 h. The mixture was then filtered, washed with water (2×5 vol) and dried under vacuum. 3-[5-Amino-4-(3-Cyanobenzoyl)-Pyrazol-1-yl]-N-Cyclopropyl-4-Methylbenzamide was obtained.

The invention claimed is:

1. A process for preparing a compound, comprising the steps of a) Reacting a compound of Formula A

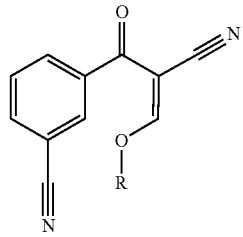

Formula A with the compound 3

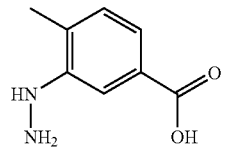

to provide the compound 5

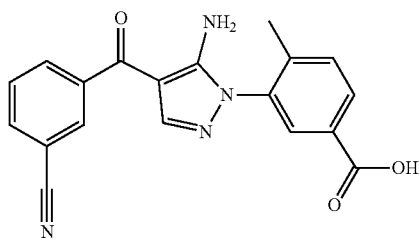

or a salt or solvate thereof; and
  b) Optionally isolating said compound 5 or a salt or solvate thereof,
wherein R is a linear or branched C1-C5 alkyl.

2. The process of claim 1, wherein R is $C_2H_5$.

3. The process of claim 1, wherein step (a) is carried out under anhydrous conditions.

4. The process of claim 1, wherein step (a) comprises adding said compound of Formula A to said compound 3 in a polar aprotic solvent, comprising at least one of the group of dimethyl sulfoxide, dimethylacetamide, dimethylformamide and N-methyl-2-pyrrolidone.

5. The process of claim 1, wherein step (a) is performed at a temperature of greater than about 90° C.; optionally further comprising the step of subsequently cooling the reaction mass.

6. The process of claim 5, further comprising the step of subsequently cooling the reaction mass to less than about 30° C.

7. The process of claim 1, further comprising the step of adding water after step (a).

8. The process of claim 1, wherein isolating said compound 5 or salt or solvate thereof comprises filtering said compound 5 or salt or solvate thereof, washing the filtrate with water and optionally drying said filtrate.

9. The process of claim 8, further comprising washing said filtrate with methanol after washing said filtrate with water.

10. The process of claim 1, further comprising the step of:
  c) Reacting said compound 5 with cyclopropylamine to provide the compound 6

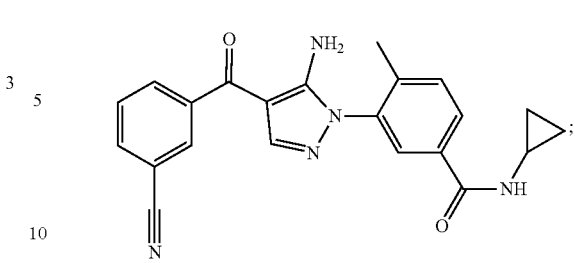

or a salt or solvate thereof.

11. The process of claim 10, wherein step (c) comprises the steps of
  a) Adding said compound 5 to a polar aprotic solvent, comprising at least one of the group of dimethyl sulfoxide, dimethylacetamide, dimethylformamide and N-methyl-2-pyrrolidone;
  b) Heating the above reaction mass to a temperature greater than about 30° C.;
  c) Optionally adding a coupling reagent in a polar aprotic solvent;
  d) Optionally purging the reaction vessel;
  e) Adding cyclopropylamine to the reaction mass;
  f) Maintaining the reaction mass to provide said compound 6 or a salt or solvate thereof;
  g) Optionally cooling, preferably the reaction mass to less than about 30° C., more preferably to about 25° C.;
  h) Optionally adding water to the reaction mass;
  i) Optionally isolating said compound 6 or a salt or solvate thereof.

12. The process of claim 11, wherein isolating said compound 6 or a salt or solvate thereof comprises filtering said compound 6 or a salt or solvate thereof, washing the filtrate with water and optionally drying said filtrate.

13. The process of claim 11, wherein said compound 6 or a salt or solvate thereof is isolated and subsequently recrystallized with a polar aprotic solvent and water mixture, wherein said polar aprotic solvent is selected from the group consisting of dimethyl sulfoxide, dimethylacetamide, dimethylformamide and N-methyl-2-pyrrolidone.

14. The process of claim 11, wherein a coupling agent is used in step c) and said coupling agent is selected from the group consisting of CDI, HOBt and HATU.

15. The compound of formula 5

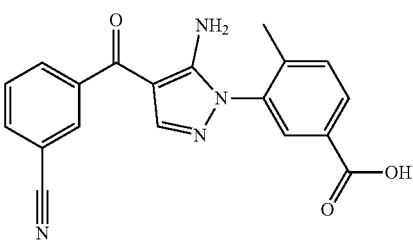

or a salt or solvate thereof obtained by the process of claim 1.

16. The compound 5

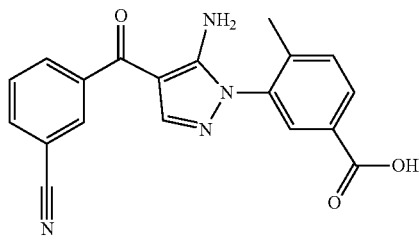

or a salt or solvate thereof.

17. A process for preparing 3-[5-Amino-4-(3-Cyanobenzoyl)-Pyrazol-1-yl]-N-Cyclopropyl-4-Methylbenzamide or a salt or solvate thereof comprising,
a. Reacting a compound of Formula A

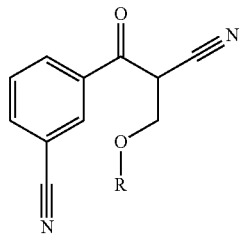

Formula A with the compound 3

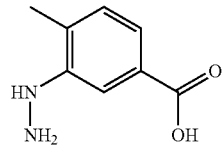

3 to provide the compound 5

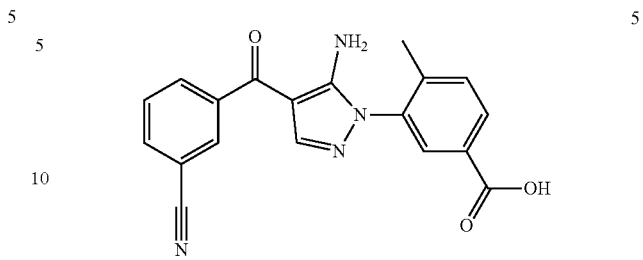

5 or a salt or solvate thereof; and b. Optionally isolating said compound 5 or a salt or solvate thereof,
c. Reacting said compound 5 or salt or solvate thereof with cyclopropylamine to provide the compound 6

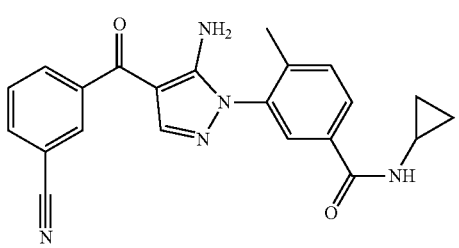

6

, or a salt or solvate thereof,
wherein R is a linear or branched C1-C5 alkyl, and wherein step c includes heating the reaction mass to a temperature of greater than about 30° C.

* * * * *